(12) United States Patent
Boruah et al.

(10) Patent No.: US 8,513,226 B2
(45) Date of Patent: Aug. 20, 2013

(54) SIMULTANEOUS METHOD FOR THE PREPARATION OF A MIXTURE OF 3-ACETOXY-17-ACETAMIDO-16-FORMYL-ANDROST-5,17-DIENE AND 3-ACETOXY-2'-CHLORO-5-ANDROSTENO[17,16-B]PYRIDINE

(75) Inventors: Romesh Chandra Boruah, Jorhat (IN); Moyurima Borthakur, Jorhat (IN); Madan Gopal Barthakur, Jorhat (IN); Paruchuri Gangadhar Rao, Jorhat (IN); Sudip Kumar Kar, Kolkata (IN); Annalakshmi Chinniah, Kolkata (IN); Suchandra Goswami, Kolkata (IN); Pratap Kumar Das, Kolkata (IN)

(73) Assignee: Council of Scientific and Industrial Research, New Delhi (IN)

(*) Notice: Subject to any disclaimer, the term of this patent is extended or adjusted under 35 U.S.C. 154(b) by 264 days.

(21) Appl. No.: 12/935,877

(22) PCT Filed: Mar. 26, 2009

(86) PCT No.: PCT/IN2009/000198
§ 371 (c)(1),
(2), (4) Date: Sep. 30, 2010

(87) PCT Pub. No.: WO2009/122435
PCT Pub. Date: Oct. 8, 2009

(65) Prior Publication Data
US 2011/0028440 A1    Feb. 3, 2011

(30) Foreign Application Priority Data
Mar. 31, 2008    (IN) .............................. 835/DEL/2008

(51) Int. Cl.
*A61K 31/565*    (2006.01)

(52) U.S. Cl.
USPC .......................... 514/170; 514/182; 514/927

(58) Field of Classification Search
USPC ......................................... 514/170, 182, 927
See application file for complete search history.

(56) References Cited

U.S. PATENT DOCUMENTS

| | | | |
|---|---|---|---|
| 4,085,135 A | 4/1978 | Kyogoku et al. | 562/464 |
| 5,374,730 A | 12/1994 | Slemon et al. | 546/273.7 |
| 5,386,032 A | 1/1995 | Brandstrom | 546/273.7 |
| 6,313,136 B1 | 11/2001 | Amin et al. | 514/300 |
| 6,953,808 B2 | 10/2005 | Gray | 514/338 |

OTHER PUBLICATIONS

Boruah et al., "Synthesis of beta-formylsteroidal enamides and their conversion into geminal dichlorides", Indian Journal of Chemistry, vol. 38B, pp. 274-282, 1999.*

Ahmed and Boruah, "An Efficient Conversion of Conjugated Oximes into Substituted Pyridines under Vilsmeier Conditions" *Tetrahedron Letters*, 37(45):8231-8232, 1996.

Bandopahyay et al., "Characteristics of a pure endogenous activator of the gastric H+,K+- ATPase system. Evaluation of the role as a possible intracellular regulator," *J Biol Chem.*, 262:5664, 1987.

Potter et aL, "Novel Steroidal Inhibitors of Human Cytochrome P450-17alpha (17alpha-Hydroxylase-C17,20-lyase): Potential Agents for the Treatment of Prostatic Cancer", J. Med. Chem., 38:2463-2471, 1995.

Berglindh, "The mammalian gastric parietal cell in vitro," *Ann. Rev. Physiol.*, 46:377-392, 1984.

Boruah et al., "Synthesis of beta-formylsteroidal enamides and their conversion into geminal dichloride," *Indian Journal of Chemistry, Section B: Organic Chemistry Including Medicinal*, 38b:274-282, 1999.

International Search Report and Written Opinion issued in PCT Patent Application No. PCT/IN2009/000198, mailed Oct. 21, 2009.

Long et aL, "Gastric antisecretory and cytoprotective activities of SCH 28080," *The Journal of Pharmacology and Experimental Tehrapeutics*, 226:114-20, 1983.

Malkov et al., "Sythesis of New Chiral 2,2'-Bipyridine Ligands and Their Application in copper catalyzed asymmetric," *Journal of Organic Chemistry*, 68:4727-4742, 2003.

Mazzeo et al., "Effects of ethanol on parietal cell membrane phospholipids and proton pump function," *Am. J. Physiol*, 254:G57, 1988.

Njar et al., "Nucleophilic vinylic "addition-elimination" substitution reaction of 3β-acetoxy-17-chloro-16-formylandrosta-5,16-diene: A novel and general route to 17-substituted steroids. Part 1—synthesis of novel 17-azolyl-Δ16 steroids; inhibitors of 17α-hydroxylase/17, 20-lyase (17α-lyase)," *Bioorganic & Medicinal Chemistry Letters*, 6:2777, 1996.

Sanui, "Measurement of inorganic orthophosphate in biological materials: extraction properties of butyl acetate," *Anal Biochem*, 60:489-504, 1974.

Senay and Levine, "Synergism between cold and restraint for rapid production of stress ulcers in rats," *Proc. Soc. Exp. Biol.*, 124:1221, 1967.

Shay et al., "A simple method for the uniform production of gastric ulceration in the rat," *Gastroenterol*, 4:43-61, 1945.

Wagner et al., "Effects of nonsteroidal antiinflammatory drugs on ulcerogenesis and gastric secretion in pylorus-ligated rat," *Dig. Dis. Sci*, 40:134-40, 1995.

* cited by examiner

*Primary Examiner* — Barbara P Badio
(74) *Attorney, Agent, or Firm* — Fulbright & Jaworski LLP (57) ABSTRACT

The present invention relates to preparation and biological evaluation of 3-acetoxy-17-acetamido-16-formyl-androst-5, 17-diene (4) and 3-acetoxy2'-chloro-5-androsteno[17,16-b] pyridine (5) as gastric proton pump inhibitor and their comparison to that of omeprazole, a clinically employed antigastric ulcer drug. Compound (4) exhibited dose dependent inhibition of histamine-stimulated acid secretion in gastric parietal cell with an $IC_{50}$ value comparable to cimetidine. No mortality or behavioral abnormality of Swiss albino mice was observed under single-dose level of 1 g/Kg body weight of compound (4). Compound (4) further exhibited excellent anti ulcer activity in vivo against indomethacin induced ulcer.

1 Claim, 6 Drawing Sheets

SIMULTANEOUS METHOD FOR THE PREPARATION OF A MIXTURE OF 3-ACETOXY-17-ACETAMIDO-16-FORMYL-ANDROST-5,17-DIENE AND 3-ACETOXY-2'-CHLORO-5-ANDROSTENO[17,16-B]PYRIDINE

This application is a national phase application under 35 U.S.C. §371 of International Application No. PCT/IN2009/000198 filed 26 Mar. 2009, which claims priority to Indian Application No. 835/DEL/2008 filed 31 Mar. 2008. The entire text of each of the above-referenced disclosures is specifically incorporated herein by reference without disclaimer.

FIELD OF THE INVENTION

The present invention relates to preparation, and biological evaluation of 3-acetoxy-17-acetamido-16-formyl-androst-5,17-diene and 3-acetoxy-2'-chloro-5-androsteno[17,16-b]pyridine as gastric antisecretory and antiulcer agents.

BACKGROUND OF THE-INVENTION

Peptic ulcer disease (PUD) is one of the most common diseases affecting GI tract. It causes inflammatory injuries in either the gastric or duodenal mucosa, with extension beyond the submucosa into the muscularis mucosa. The traditional medical approach to treating ulcers is with antacids, $H_2$ receptor blockers and proton pump inhibitors. Cimetidine, famotidine, nizatidine and ranitidine are examples of $H_2$ receptor blockers. Proton pump inhibitors (PPIs) are one of the most commonly prescribed classes of medicines in the primary care setting and are often used in the treatment of acid-peptic diseases. The PPIs reduce the production of acid by inhibiting the enzyme hydrogen-potassium adenosine triphosphatase ($H^+,K^+$-ATPase) of the gastric parietal cell that produces acid. The proton pump is the terminal stage in gastric acid secretion and it is responsible for secreting $H^+$ ions into the gastric lumen. The lack of acid in the stomach aids in healing duodenal ulcers. Omeprazole (Prilosec) is a proton pump inhibitor, which blocks the production of acid by the stomach. Several other PPIs such as lansoprazole, rabeprazole, pantoprazole and esomeprazole have been introduced in the clinical practice. However anti-ulcer drugs may increase certain allergies to food. All the PPIs under clinical practice include non-steroidal drugs.

On the other hand, the steroidal aza heterocycles are well known as inhibitors of enzymes such as 5α-reductase and 17α-lyase. Moreover, the steroidal heterocycles such as danazol, deflazacort, cortivazol, nevazol, 2-azasteroid and finasteride, attract much attention due to their biological activities against various ailments like benign prostatic hyperplasia, asthma, 5α-reductase inhibitor, prostate cancer and L-1210 leukemia. However, the biological activity of the steroidal compounds as PPI is not yet known.

Reference may be made to A E Brandstorm US patent 1995, U.S. Pat. No. 5,386,032 wherein, an improved method for the synthesis of 5-methoxy-2-[(4-methoxy-3,5-dimethyl-2-pyridinyl)-methyl]sulfinyl-1H-benzimidazole (omeprazole) by reacting 5-methoxy-2-[(4-methoxy-3,5-dimethyl-2-pyridinyl)-methylthio]-1H-benzimidazole with m-chloroperoxy benzoic acid has been reported in a methylene chloride solution at pH 8.0 to 8.6 followed by addition of alkyl formate.

Another reference may be made to C Slemon & B Marcel US patent 1994, U.S. Pat. No. 5,374,730, wherein, omeprazole and lansoprazole are produced from the corresponding acetate-sulfide compounds by a process of oxidation to form the amide sulfinyl compound, followed by alkaline hydrolysis to the sulfinyl carboxylate or salt and decarboxylation.

Still another reference may be made to K Kyogoku, K Hatayama, S Yokomori, J Sawada and I Tanaka US patent 1978 U.S. Pat. No. 4,085,135, wherein preparation of 2'-(carboxymethoxy)-chalcones having anti-gastric and anti-duodenal ulcer activities has been described.

Still another reference may be made to K Amin, M Dahlstrom, P Nordberg & I Starke US Patent 2001, U.S. Pat. No. 6,313,136 wherein, substituted imidazo pyridine derivatives have been reported to inhibit gastric acid secretion and thus can be used in the prevention and treatment of gastrointestinal inflammatory diseases.

Still another reference may be made to N M Gray US patent 2005, U.S. Pat. No. 6,953,808 wherein, optically pure (−)-pantoprazole has been employed for the treatment of gastroduodenal ulcers in human while substantially reducing the concomitant liability of adverse effects associated with the racemic mixture of pantoprazole.

Still another reference may be made to V C O Njar, G T Klus & A M H Brodie, *Bioorg. Med. Chem. Lett.* 1996, 6, 2777 wherein, steroidal 17-imidazolyl- and triazolyl-derivatives have been prepared as candidates for 17-lyase inhibitors.

Still another reference may be made to G A Potte, S E Bane, M Jarman & M G Rowlands, *J. Med. Chem.* 1995, 38, 2403 wherein, steroidal 17-pyridyl derivative (abiraterone) have been reported as active candidate for 17-lyase inhibitors.

OBJECTS OF THE INVENTION

The main objective of the present invention is to prepare and study 3-acetoxy-17-acetamido-16-formyl-androst-5,17-diene (4) and 3-acetoxy-2'chloro-5 Androsteno[17,16-b]pyridine (5) as potential gastric antisecretory and antiulcer agents.

Another objective of the present invention is to prepare 3-acetoxy-17 acetamido-16-formyl-androst-5,17-diene (4) and 3-acetoxy-2'chloro-5-androsteno[17,16-b]pyridine (5) from Vilsmeier formylation of 3-acetoxy-17-acetamido-androst-5,17-diene (3).

Another objective of the present invention is to synthesize 3-acetoxy-17-acetamido-androst-5,17-diene (4) and 3-acetoxy-2'chloro-5-androsteno[17,16-b]pyridine (5) from Beckmann rearrangement of 16-dehydropregnenolone acetate-oxime.

Still another objective of the present invention is to evaluate the $H^+,K^+$-ATPase inhibition activities of 4, and 5 in comparison to commercially available anti-gastric ulcer drug omeprazole.

Still another objective of the present invention is to evaluate the nature of inhibition of $H^+,K^+$-ATPase by Compound 4.

Still another objective of the present invention is to study 3-acetoxy-17-acetamido-16-formyl-androst-5,17-diene (4) as inhibitor of histamine-stimulated gastric acid secretion.

Still another objective of the present invention is to evaluate the inhibition of histamine-stimulated acid secretion activity of 4 in comparison to commercially available anti-gastric ulcer drug cimetidine and omeprazole.

Still another objective of the present invention is to evaluate the in vivo potential of compound 4 to inhibit cold restraint stress induced ulcer in rats in comparison to commercially available anti-gastric ulcer drug cimetidine.

Still another objective of the present invention is to evaluate the in vivo potential of compound 4 to inhibit gastric acid secretion in pylorus ligated rats in comparison to commercially available anti-gastric ulcer drug cimetidine.

Still another objective of the present invention is to evaluate the in vivo potential of compound 4 to inhibit indomethacin-induced ulcer in rats in comparison to commercially available anti-gastric ulcer drug omeprazole.

SUMMARY OF THE INVENTION

The present invention relates to biological evaluation of 3-acetoxy-17-acetamido-16-formyl-androst-5,17-diene (4) and 3-acetoxy-2'-chloro-5-androsteno[17,16 b]pyridine (5) as gastric antisecretory and antiulcer agent.

Figure 1:
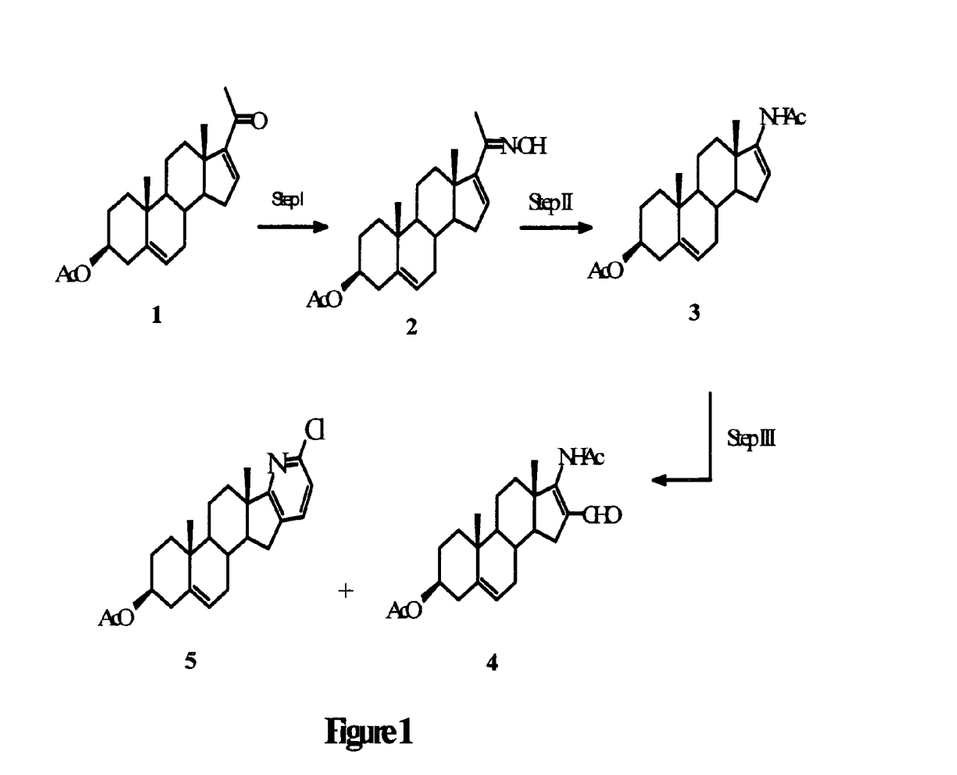
FIG. 1 illustrates the method of preparation of compounds 4 and 5 The preparation involves oximation of 16-DPA (1) to 16-dehydropregnenoloneacetate-oxime (2) as shown step 1, Beckmann rearrangement of compound of formula (2) to 3-acetoxy-17-acetamido-androst-5,17-diene (3) as shown by step II, followed by Vilsmeier reaction of compound of formula (3) to 3-acetoxy-17-acetamido-16-formyl-androst-5,17-diene (4) and 3-acetoxy-2'chloro-5-androsteno[17,16-b]pyridine (5) as shown by step III.

The preparation involves oximation of 16-DPA (1) to 16-dehydropregnenoloneacetate-oxime (2), Beckmann rearrangement of 2 to 3-acetoxy-17-acetamido-androst-5,17-diene (3), followed by Vilsmeier reaction of 3 to 3-acetoxy-17-acetamido-16-formyl-androst-5,17-diene (4) and 3-acetoxy-2'chloro-5-androsteno[17,16-b]pyridine (5) (FIG. 1).

BRIEF DESCRIPTION OF THE DRAWINGS

FIG. 1.

DETAILED DESCRIPTION OF THE INVENTION

Accordingly the present invention provides a simultaneous method for the preparation of a mixture of 3-acetoxy-17-acetamido-16-formyl-androst-5,17-diene (4) and 3-acetoxy-2'-chloro-5-androsteno[17,16-b]pyridine (5) from 16-dehydro pregnenolone acetate (1) and the said process comprising the steps of:

(a) reacting 16-dehydropregnenolone acetate of formula 1 with hydroxylamine hydrochloride and potassium dihydrogen phosphate in a protic solvent, under reflux for a period of 1-2 hrs, followed by the removal of solvent and neutralization of the resultant mass with sodium bicarbonate to obtain product 16-dehydropregnenolone-3-acetate-20-oxime of formula 2, treating 16-dehydropregnenolone acetate-oxime (2) with Vilsmeier reagent in chloroform directly, at a temperature of 0-10° C., for a period of 2-4 hrs, followed by neutralization and extraction with chloroform and washing with water, followed by drying and removing the solvent to obtain the desired product of 3-acetoxy-17-acetamido-16-formyl-androst-5,17-diene (4) and 3-acetoxy-2'chloro-5-androsteno[17,16-b]pyridine (5) or reacting the above said compound of formula 2 with phosphorous oxychloride, under stirring, at a temperature of 1-15° C. to obtain 3-acetoxy-17-acetamido-androst-5,17-diene of formula 3 as beckmann rearranged product and reacting the above said compound 3-acetoxy-17-acetamido-androst-5,17-diene of formula 3 with a mixture of phosphorous oxychloride and dimethylformamide, at a temperature of 5-25° C., for a period of 2-4 hrs and quenching the reaction mixture in water to obtain a mixture of 3-acetoxy-17-acetamido-16-formyl-androst-5,17-diene (4) end 3-acetoxy-2'chloro-5-androsteno[17,16-b]pyridine (5), followed by neutralization and extraction with chloroform and washing with water followed by drying and removing the solvent to obtain the desired mixture of 3-acetoxy-17-acetamido-16-formyl-androst-5,17-diene (4) and 3-acetoxy-2'chloro-5-androsteno[17,16-b]pyridine (5)

In another embodiment of the present invention the process further comprises separating the compounds 4 and 5 from the mixture as obtained in step b In another embodiment of the invention the separation of the compounds from the mixture is done by any known method in the art.

In a yet another embodiment the preferable method of separation is column chromatography over silica gel.

In an embodiment of the invention, wherein the 16-dehydropregnenolone acetate of, formula 1 used is of commercial grade.

In another embodiment of the invention wherein the protic solvent used in step (a) is ethanol.

In a further embodiment of the invention, wherein the yield of 16-dehydropregnenolone-3-acetate-20-oxime of formula 2 obtained in step (a) is in the range of 80-90%.

In an embodiment of the invention, wherein the yield of 3-acetoxy-17-acetamido-16-formyl-androst-5,17-diene (4) obtained in step (b) is in the range of 65-85%.

In an embodiment of the invention, wherein the yield of 3-acetoxy-2'chloro-5-androsteno[17,16-b]pyridine (5) obtained in step (b) is in the range of 80-90%.

In an embodiment of the present invention, the steroidal intermediate 16-DPA (1) could be converted into corresponding conjugated oxime (2) in high yields.

In another embodiment of the present invention, the enamide 3-acetoxy-17-acetamido-androst-5,17-diene (3) could be derived from corresponding steroidal conjugated oximes 2 by treatment with phosphorous oxychloride.

Still in another embodiment of the invention, the Vilsmeier reaction of steroidal enamides (3) afforded 3-acetoxy-17- acetamido-16-formyl-androst-5,17-diene (4) and 3-acetoxy-2'chloro-5-androsteno[17,16-b]pyridine (5) at ambient temperature.

In yet another embodiment of present invention use of compounds 4 or 5 or a mixture thereof as gastric anti secretory and or anti ulcer agent.

In a yet another embodiment the present invention also relates to a pharmaceutical composition comprising compound 4 or 5 or a mixture thereof with a pharmaceutical adjutants or carrier.

In an embodiment of the present invention, steroidal derivatives 4 and 5 have shown anti $H^+,K^+$-ATPase activity similar to benzimidazole derivatives such as omeprazole, lansoprazole, pantoprazole or esomeprazole.

In another embodiment of the present invention, the anti-$H^+,K^+$-ATPase activity of 4 and 5 were compared with antigastric ulcer drug omeprazole in vitro.

In another embodiment of the present invention, the inhibition of $H^+,K^+$-ATPase by the Compound 4 was demonstrated to be irreversible in nature, like omeprazole, lansoprazole, pantoprazole or esomeprazole.

Still in another embodiment of the present invention, pig gastric membranes enriched in apical and tubulovesicular membranes were used for the evaluation of anti-$H^+,K^+$-ATPase activity of 4 and 5.

Figure 2:
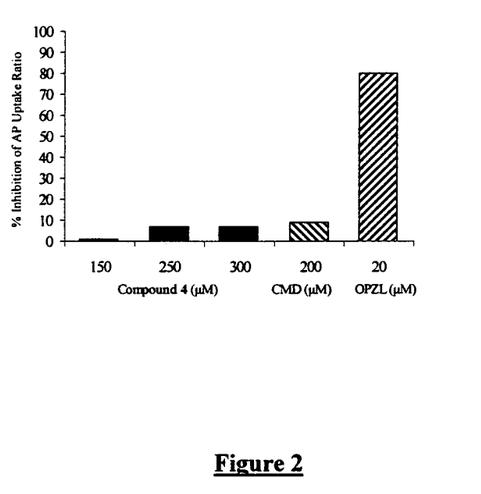
FIG. 2: Effect of Compound 4 on basal acid secretion in gastric parietal cell. Dose-dependent inhibition of aminopyrine (AP) uptake ratio was measured after treatment of parietal cell suspension ($5 \times 10^6$ cells) with compound 4 for 1 h at the indicated concentrations. CMD:cimetidine; OPZL:omeprazole. The data represent averages of 2-3 determinations each carried out in triplicate.

Still in another embodiment of the present invention, the effect of varied concentrations of Compound 4 on basal acid secretion in freshly prepared rabbit gastric parietal cells was examined. The basal acid secretion was found to decrease only marginally upon exposure to increasing concentrations of Compound 4 (FIG. 2). Under identical experimental conditions, the $H_2$ receptor antagonist cimetidine (200 μM) produced about same extent of inhibition (only ~10%) as was noted with highest concentration of Compound 4 (300 μM). In contrast, omeprazole, an $H^+,K^+$-ATPase inhibitor, produced strong inhibition (80-90%) of basal acid secretion at 20 μM dose.

Figure 3:
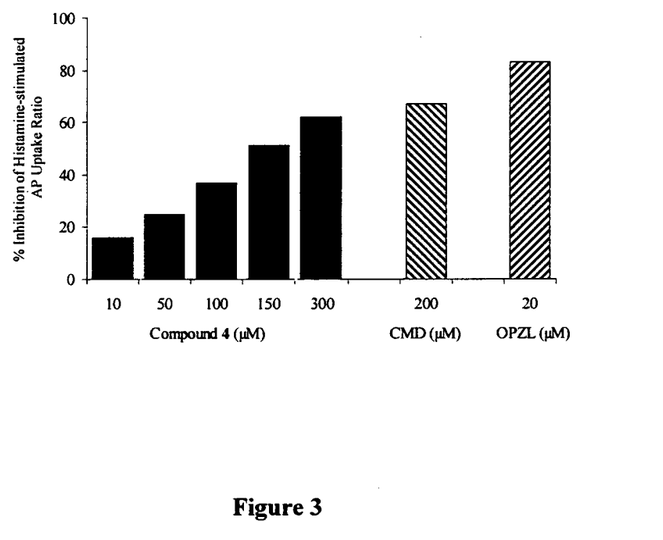
FIG. 3: Effect of Compound 4 on histamine-stimulated (0.1 mM) acid secretion in gastric parietal cell. Dose-dependent inhibition of aminopyrine (AP) uptake ratio was measured after treatment of parietal cell suspension ($5 \times 10^6$ cells) with Compound 4 for 1 h at the indicated concentrations. Histamine-stimulated AP uptake ratio was considered as 100%. CMD:cimetidine; OPZL:omeprazole. The data represent averages of 2-3 determinations each carried out in triplicate.

Still in another embodiment of the present invention, the Compound 4 was further examined for its effect on histamine stimulated (0.1 mM) acid secretion in freshly prepared rabbit gastric parietal cells. It exhibited a dose-dependent inhibition of histamine-stimulated acid secretion (FIG. 3) with an $IC_{50}$ value of about 130 μM. The compound 4 was found to be almost equiactive as compared with cimetidine in inhibiting histamine-stimulated secretion. Omeprazole at the same low dose of 20 μM nevertheless produced similar strong inhibition of histamine-stimulated acid secretion like basal acid secretion.

In another embodiment of the present invention, the anti ulcer activity of compound 4 was probed against cold restraint stress ulcer model in rat. The compound 4 exhibited potent antiulcer activity in vivo at 50 mg/kg body wt.

In another embodiment of the present invention, the antisecretory activity of compound 4 was investigated against pylorus ligation induced ulcer model in rat. The compound 4 exhibited mild reduction in acid output (~33% inhibition) in vivo at 50 mg/kg body weight.

Still in another embodiment of the present invention, the antiulcer activity of compound 4 was studied in vivo against indomethacin-induced ulcer model in rat. The compound exhibited potent anti ulcer activity at 10-50 mg/kg b.w. and is comparable to the activity of 5 mg/kg omeprazole.

Still in another embodiment of the present invention, the Vilsmeier reaction of steroidal enamides (1) afforded 3-acetoxy-17-acetamido-16-formyl-androst-5,17-diene (4) and 3-acetoxy-2'chloro-5-androsteno[17,16-b]pyridine (5) at ambient temperature.

A yet another embodiment of the present invention propose use of compounds 4 or 5 or a mixture thereof as gastric anti secretory and or anti ulcer agent.

In yet another embodiment the present invention relates to a pharmaceutical composition comprising compound 4 or 5 or a mixture thereof with a pharmaceutical adjutants or carrier.

Accordingly, the present invention provides biological evaluation of 3-acetoxy-17-acetamido-16-formyl-androst-5,17-diene (4) and 3-acetoxy-2'-chloro-5-androsteno[17,16-b]pyridine (5) as gastric antisecretory and antiulcer agent.

The first step of the synthesis involved oximation reaction of 16-dehydropregnenolone acetate (1) with hydroxylamine hydrochloride to 16-dehydropregnenolone-3-acetate-20-oxime (2). In the second step, a solution of 2 was treated with phosphorous oxychloride to obtain 3-acetoxy-17-acetamido-androst-5,17-diene (3) as Beckmann rearranged product. In the third step, a mixture of phosphorous oxychloride and dimethylformamide was treated with 3 at ambient temperature to afford a mixture of 3-acetoxy-17-acetamido-16-formyl-androst-5,17-diene (4) and 3-acetoxy-2'chloro-5-androsteno[17,16-b]pyridine (5).

The following examples are given by illustrations and should not construed the scope of the invention.

Example-I

Preparation 16-dehydropregnenolone acetate-20-oxime (2)

To a solution of compound of formula 1 (2.0 mmol) in ethanol (20 ml) was added hydroxylamine hydrochloride (5.0 mmol) and potassium dihydrogen phosphate (5.0 mmol) and the reaction mixture was refluxed for 1 h. Removal of the solvent and neutralization with sodium bicarbonate gave a solid mass, which on recrystallization from methanol afforded oxime 2, yield 0.94 g (90%), m.p. 200° C.

3-Acetoxy-17-acetamido-androst-5,17-diene (3)

16-Dehydropregnenolone acetate-20-oxime (2) (3.0 mmol) was dissolved in phosphorous oxychloride (6 ml) and stirred at 5° C. The reaction mixture was poured into water, neutralized and extracted with ether. Washing of the organic portion with water, drying over anhydrous sodium sulfate and removal of the solvent afforded 3 as a solid product, which was employed in the following step without purification.

Preparation 3-acetoxy-17-acetamido-16-formyl-androst-5,17-diene (4) and 3-acetoxy-2'chloro-5-androsteno[17,16-b]pyridine (5) by Vilsmeier reaction of compound of formula 3

0.55 g of 3-acetoxy-17-acetamido-androst-5,17-diene (3) in chloroform was treated with a mixture of phosphorous oxychloride and dimethyl formamide at 10° C. for 4 h. The reaction mixture was quenched in water, neutralized with saturated sodium bicarbonate solution and extracted with chloroform, washed with water, dried and solvent removed to afford a mixture of products which were purified by column chromatography over silica gel to obtain compound 4 and 5 in 65% and 27% yields respectively. Compound 4: yield 65%, mp 236° C., IR (KBr) v 3338, 2940, 1732, 1625, 1600, 1500 cm$^{-1}$; $^1$HNMR (CDCl$_3$) δ 10.80 (bs, 1H), 9.50 (s, 1H), 9.18 (s, 1H), 5.19 (bs, 1H), 4.40 (m, 1H), 2.02 (s, 3H), 1.90 (s, 3H), 0.98 (s, 3H), 2.35-1.20 (17H, m); Mass spectra: m/z 399 (M$^+$). Compound 5: yield 27%, mp 200° C., $^1$HNMR (CDCl$_3$) δ 7.11 (d, 1H, J=8 Hz), 6.76 (d, 1H, J=8 Hz), 5.20 (bs, 1H), 4.35 (m, 1H), 1.90 (s, 3H), 1.05 (s, 3H), 2.67-1.15 (17H, m); IR (KBr) v 2960, 1725, 1562, 1412 cm$^{-1}$; Mass spectra: m/z 399 (M$^+$).

Example-II

Preparation 16-dehydropregnenolone acetate-20-oxime (2)

To a solution of 1 (4.0 mmol) in ethanol (40 ml) was added hydroxylamine hydrochloride (10.0 mmol) and potassium dihydrogen phosphate (10.0 mmol) and the reaction mixture was refluxed for 1 h. Removal of the solvent and neutralization with sodium bicarbonate gave a solid mass, which on recrystallization from methanol afforded oxime 2, yield 0.93 g (90%), m.p. 200° C.

3-Acetoxy-17-acetamido-androst-5,17-diene (3)

16-Dehydropregnenolone acetate-20-oxime (2) (6.0 mmol) was dissolved in phosphorous oxychloride (12 ml) and stirred at 5° C. The reaction mixture was poured into water, neutralized and extracted with ether. Washing of the organic portion with water, drying over anhydrous sodium sulfate and removal of the solvent afforded compound of formula 3 as a solid product, which was employed in the following step without purification.

Preparation 3-acetoxy-17-acetamido-16-formyl-androst-5,17-diene (4) and 3-acetoxy-2'chloro-5-androsteno[17,16-b]pyridine (5) by Vilsmeier reaction of 3

1.11 g of 3-acetoxy-17-acetamido-androst-5,17-diene (3) in chloroform was treated with a mixture of phosphorous oxychloride and dimethyl formamide at 10° C. for 5 h. The reaction mixture was quenched in water, neutralized with saturated sodium bicarbonate solution and extracted with chloroform, washed with water, dried and solvent removed to afford a mixture of products which were purified by column chromatography over silica gel. Compound 4: yield 66%, mp 236° C. and Compound 5: yield 18%, mp 201° C.

Example-III

Preparation 16-dehydropregnenolone acetate-20-oxime (2)

To a solution of compound of formula 1 (4.0 mmol) in ethanol (40 ml) was added hydroxylamine hydrochloride (10.0 mmol) and potassium dihydrogen phosphate (10.0 mmol) and the reaction mixture was refluxed for 1 h. Removal of the solvent and neutralization with sodium bicarbonate gave a solid mass, which on recrystallization from methanol afforded oxime 2, yield 0.93 g (90%), m.p. 200° C.

3-Acetoxy-17-acetamido-androst-5,17-diene (3)

16-Dehydropregnenolone acetate-20-oxime 2 (12.0 mmol) was dissolved in phosphorous oxychloride (25 ml) and stirred at 5° C. The reaction mixture was poured into water, neutralized and extracted with ether. Washing of the organic portion with water, drying over anhydrous sodium sulfate and removal of the solvent afforded 3 as a solid product, which was employed in the following step without purification.

Preparation 3-acetoxy-17-acetamido-16-formyl-androst-5,17-diene (4) and 3-acetoxy-2'chloro-5-androsteno[17,16-b]pyridine (5) by Vilsmeier reaction of 3

4.22 g of 3-acetoxy-17-acetamido-androst-5,17-diene (3) in 60 ml of chloroform was treated with a mixture of phosphorous oxychloride (55 ml) and dimethyl formamide (55 ml) at 10° C. for 2-4 h. The reaction mixture was quenched in water, neutralized with saturated sodium bicarbonate solution and extracted with chloroform (3×20 ml), washed with water, dried and solvent removed to afford a mixture of products which were purified by column chromatography over silica gel. Compound 4: yield 65%, mp 235° C. and Compound 5: yield 20%, mp 200° C.

In Vitro Biological Evaluation of 3-acetoxy-17-acetamido-16-formyl-androst-5,17-diene (4) and 3-acetoxy-2'chloro-5-androsteno[17,16-b]pyridine (5) for Proton Pump Inhibition Activity Pig gastric membranes enriched in apical and tubulovesicular membranes were prepared as described in the literature (S Bandopadhyay, P K Das, M V Wright, J Nandi, D Bhattacharya & T K Ray, J. Biol. Chem. 1987, 262, 5664). The fundic mucosal regions of pig stomach were desquamated and scrapped to collect oxyntic cell-riched fractions. The homogenized tissue was centrifuged at 5000×g for 8 min, the supernatant was layered over 37% sucrose and centrifuged at 100,000×g for 4½ h. The major membrane band appeared in the interface was collected, diluted with homogenizing buffer and recentrifuged at 110,000×g for 90 min. The pellet containing H$^+$,K$^+$-ATPase rich apical and tubulovesicular membranes was suspended in appropriate buffer and stored at −80° C. for use as the source of enzyme. Such membranes show K$^+$-stimulated H$^+$-transporting ATPase activity, which could be specifically blocked by omeprazole, an irreversible inhibitor of gastric H$^+$,K$^+$-ATPase.

The H$^+$,K$^+$-ATPase activity was measured at 37° C. in a 1 ml reaction mixture containing 2 mM MgCl$_2$, 2 mM ATP, 10 mM PIPES (pH 6.8), 20 mM KCl and 10-15 μg membrane protein. The assay mixture was preincubated for 15 min in presence of different concentrations of 4, 5 or omeprazole before initiating the reaction with ATP. After incubation for 10 min, the reaction was terminated by addition of 1 ml ice-chilled TCA (14%).

K$^+$-stimulated activity, referred to as H$^+$,K$^+$-ATPase, was calculated as the difference between the activity in presence of Mg$^{+2}$ plus K$^+$ and basal activity (Mg$^+$-ATPase) in presence of Mg$^{+2}$ alone. The membrane showed high K$^+$-stimulated activity of around 40-50□moles P$_i$/mg/h with basal activity of only around 10 μmoles Pi/mg/h. The liberated inorganic phosphate was quantitated according to a reported procedure (H Sanui, Anal. Biochem. 1974, 60, 489) and the effects of 4 and 5 were assessed. The effects are quantitated in terms of percent inhibition of H$^+$,K$^+$-ATPase activity, and compared with that of omeprazole.

Gastric proton pump (H$^+$,K$^+$-ATPase) inhibition activity of the 3-acetoxy-17-acetamido-16-formyl-androst-5,17-diene (4) and 3-acetoxy-2'chloro-5-androsteno[17,16-b]pyridine (5) at 1 μM, 5 μM, 10 μM and 100 μM concentration range were compared in vitro with omeprazole (Table 1). The standard drug omeprazole, under similar experimental condition showed about 20-80% inhibition in the concentration range 3 μM and 30 μM. Whereas the inhibition of H$^+$,K$^+$-ATPase by 5 was found to be nominal, the activity of 4 was encouraging as gastric proton pump inhibitor. The inhibition of H$^+$,K$^+$-

ATPase by 4 was observed to be dose dependent. The calculated $IC_{50}$ values were 18 μM for and approximately 6 μM for omeprazole which may be taken to mean that omeprazole is about three times more potent than 4. The nature of inhibition of $H^+,K^+$-ATPase by the Compound 4 was investigated in some details. Differential degree of inhibition at a fixed concentration of the Compound 4 (10 μM) against different concentrations of the $H^+,K^+$-ATPase-rich proteins (5 and 20 μg) indicated that the inhibition is irreversible in nature (see Table 2). In another experiment, the membrane bound enzyme was pretreated with the Compound 4 (10 μM) for 0 and 30 min (Table 3) prior to initiation of the enzymatic reaction with the substrate ATP. The higher degree of inhibition due to greater time of exposure of the enzyme with the compound 4 provided further evidence that the molecule is acting as irreversible inhibitor, like omeprazole which is known to be an irreversible inhibitor of gastric $H^+,K^+$-ATPase.

TABLE 1

Anti Gastric Proton Pump activity of 4 and 5

| Compound | Molecular Weight | Concentration (μM) | % Inhibition $H^+, K^+$-ATPase | Comment |
|---|---|---|---|---|
| Omeprazole | 364 | 3 | 20 | Strongly active +++ |
|  |  | 30 | 80 |  |
| 4 | 399 | 1 | 7 | Strongly active +++ |
|  |  | 5 | 20 |  |
|  |  | 10 | 47 |  |
|  |  | 100 | 75 |  |
| 5 | 399 | 1 | 2 | Active ++ |
|  |  | 10 | 37 |  |
|  |  | 100 | 57 |  |

TABLE 2

Percent inhibition of $H^+, K^+$-ATPase activity at different protein to inhibitor ratio

| Sample | Protein Concentration | % Inhibition of $H^+, K^+$-ATPase | Observation |
|---|---|---|---|
| 4 (10 μM) | 5 μg/assay | 75 | Irreversible Inhibition |
|  | 20 μg/assay | 57 |  |

TABLE 3

Percent inhibition of $H^+, K^+$-ATPase activity as a function of preincubation time

| Sample | Preincubation time (min) | % Inhibition of $H^+, K^+$-ATPase | Observation |
|---|---|---|---|
| 4 (10 μM) | 0 | 2 | Irreversible Inhibition |
|  | 30 | 56 |  |

In Vitro Biological Evaluation of 3-acetoxy-17-acetamido-16-formyl-androst-5,17-diene (4) for Antisecretory Activity in Gastric Parietal Cells Parietal cells (PC) were isolated from New Zealand White rabbits (weighing 2.5 kg) essentially according to Berglindh (T Berglindh, *Ann. Rev. Physiol*. 1984, 46, 377) and as modified by Mazzeo et al. (A R Mazzeo, J Nandi & R A Levine, *Am. J. Physiol*. 1988, 254, G57). Briefly, the technique involves high-pressure perfusion of the stomach in live animal with oxygenated PBS, stripping and mincing the mucosa followed by 2-step proteolytic digestion at 37° C., first with a mixture of protease (0.1 mg/ml) and pronase (1 mg/ml) for 15 min and then the pellet obtained therefrom with collagenase (1 mg/ml) for 30 min. The washed cell pellet containing majority of the gastric cells was layered on top of a two-step gradient of Nycodenz (density 1.05 and 1.075 g/ml) and centrifuged at 150×g for 10 min. Parietal cells enriching in between density of 1.05 and 1.075 interface were collected, washed 3 times with respiratory medium and used for the study. The PC preparations were nearly 90% pure and viable.

The effect of Compound 4 on basal and histamine-stimulated acid secretion in parietal cells was examined as follows. The PC suspension was preincubated for 60 min in the presence and absence of different concentrations of Compound 4 at 37° C. with gentle stirring and continuous slow top gassing with oxygen. The [$^{14}$C]-aminopyrine (115 μCi/mM) was added to the suspension at a concentration of 0.1 mCi/ml, and incubation was continued for another 10 min. One-milliliter aliquots of such PC suspension (~5×10$^6$ cells) were further incubated in the presence and the absence of histamine (0.1 mM) for 20 min at 37° C. with slow shaking and oxygen top gassing. At the end of the incubation, the PC suspensions were centrifuged, supernatant carefully aspired off and the pellets solubilized in scintillation fluid containing Triton X-100. The resulting solution was counted in a liquid scintillation counter. The aminopyrine accumulation was determined as the ratio of intra- to extracellular aminopyrine according to Mazzeo et al. (A R Mazzeo, J Nandi & R A Levine, *Am. J. Physiol*. 1988, 254, G57).

The basal acid secretion was found to decrease only marginally upon exposure to increasing concentrations of Compound 4 (FIG. 2). Under identical experimental conditions, the $H_2$ receptor antagonist cimetidine (200 μM) produced about same extent of inhibition (only ~10%) as was noted with highest concentration of Compound 4 (300 μM). In contrast, omeprazole, an $H^+,K^+$-ATPase inhibitor, produced strong inhibition (80-90%) of basal acid secretion at 20 μM dose.

The Compound 4 was further examined for its effect on histamine stimulated (0.1 mM) acid secretion in rabbit gastric parietal cells. It exhibited a dose-dependent inhibition of histamine-stimulated acid secretion (FIG. 3) with an $IC_{50}$ value of about 130 μM. The compound 4 was found to be almost equiactive as compared with cimetidine in inhibiting histamine-stimulated secretion. Omeprazole at the same low dose of 20 μM nevertheless produced similar strong inhibition of histamine-stimulated acid secretion like basal acid secretion.

Single-dose Acute Toxicity Evaluation of 3-acetoxy-17-acetamido-16-formyl-androst-5,17-diene (4)

The Compound 4 was checked for mortality of the Swiss albino mice. Five animals of Swiss albino mice strain were used for this purpose. The dosage up to 1 g/kg body weight was given orally per mice and the animals kept up to 15 days under observation. It was observed that the mice were not affected at the dose level of 1 g/kg body weight of Compound 4. No mortality and behavioral abnormality was noted under such single-dose acute toxicity evaluation study.

Figure 4:
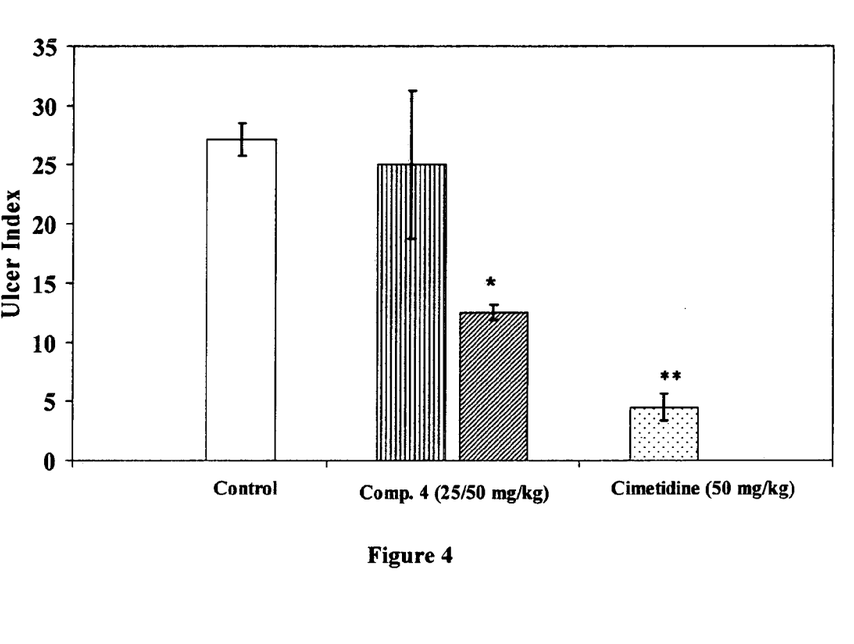
FIG. 4: Effect of compound 4 on cold restraint stress ulcer in rats. Animals were divided into four groups. Data represent the mean±SEM (n=6). Student's unpaired t-test was carried out to evaluate the statistically significant difference of the mean of the treated group from that of the untreated control. * $P<0.05$ vs. control, ** $P<0.01$ vs. control.

In Vivo Effect of 3-acetoxy-17-acetamido-16-formyl-androst-5,17-diene (4) on Cold Restraint Stress Induced Ulceration Adult rats of either sex, weighing about 200 g were fasted for 24 h with free access to water. Compound 4 (in 0.4% hydroxypropylmethylcellulose, HPMC) were administered 45 min before immobilizing the animals. The rats were immobilized in the restraint cage at 4 °C for 4 h and were sacrificed immediately after the restraint period according to the method of Senay and Levine (E C Senay & R J Levine, *Proc. Soc. Exp. Biol. Med.* 1967, 124, 1221). The abdomen was cut opened, stomach taken out and incised along the greater curvature to observe the gastric lesions. The ulceration was rated and the ulcer index (UI) scored as described in Wagner et al. (K Wagner, J Nandi, R L King & R A Levine, *Dig. Dis. Sci.* 1995, 40, 134), the effect of compound 4 being expressed graphically as a function of ulcer index and the result was further expressed as the percent protection of the ulcer formation in comparison to the untreated control group (FIG. 4).

Compound 4 exhibited 54% protection of ulceration as induced by cold restraint stress at 50 mg/kg body weight dose. Cimetidine under identical experimental condition induced 86% protection at 50 mg/kg dose.

In Vivo Effect of 3-acetoxy-17-acetamido-16-formyl-androst-5,17-diene (4) on Gastric Secretion in Pylorus-ligated Rats The pylorus of each rat was ligated under anesthesia according to the method of Shay et. al. (H Shay, S A Komarov, S S Fels, D Merange, M Grunstein & H Siplet, *Gastroenterol.* 1945, 4, 43). Each of the animals were then allowed to stand abstained from food and water in a cage. After 4 h, the animals were sacrificed and the stomachs were removed. The gastric contents were collected and centrifuged, and the secretory volume, pH and acid content of the supernatants were measured. The acid content was measured by titrating to pH 7.0 with 0.01 N NaOH using an autotitrator (Metrohm). The total acid content of the drug treated groups was compared to that of control groups, presented graphically in FIG. 5 and thereby, the reduction percentage of acid content was calculated. Compound 4 was suspended in 0.4% HPMC and administered orally at graded dose (10, 20, 50 and 100 mg/kg dose) in different groups 45 min before the ligation. In the control group, the vehicle (0.4% HPMC) was administered.

Figure 5:
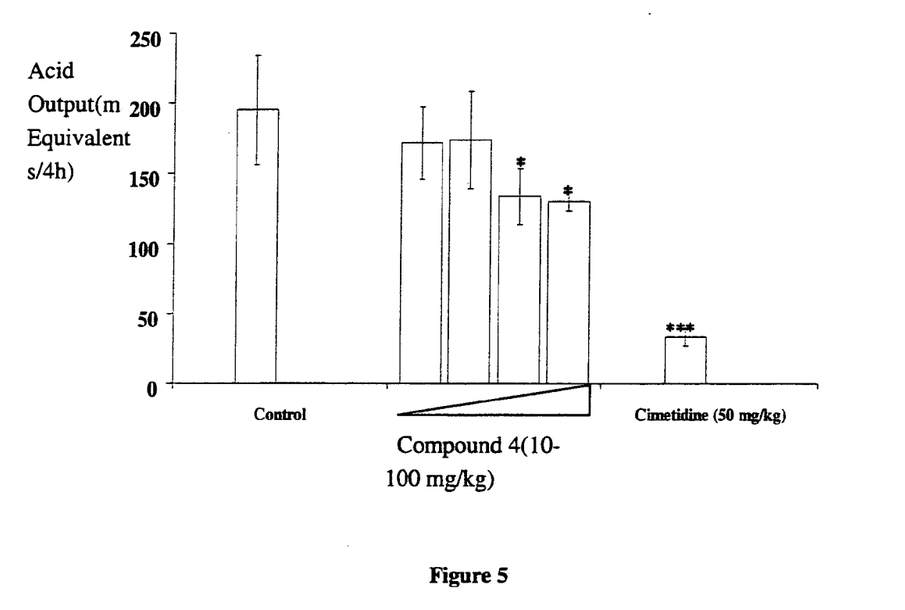
FIG. 5: Antisecretory effect of compound 4 in pylorus-ligated rats. Animals were divided into six groups. Data represent the mean±SEM (n=6). Student's unpaired t-test was carried out to evaluate the statistically significant difference of the mean of treated group from that of the untreated control. * $P<0.05$ vs. control,  $P<0.01$ vs. control, * $P<0.001$ vs. control.

As described in FIG. 5, compound 4 exhibited ~30% inhibition of acid output in pylorus-ligated rat at 50-100 mg/kg dose. Cimetidine under identical experimental condition exhibited ~80% inhibition of acid secretion at 50 mg/kg dose.

In Vivo Effect of 3-acetoxy-17-acetamido-16-formyl-androst-5,17-diene (4) on Indomethacin-induced Ulcer in Rat The animals were kept fasting for 24 h before initiating the experiment, drinking water being available ad libitum. The animals were allotted to three groups, each group comprising of six rats. Ulcerations were created by administering 15 mg/kg p.o. doses of indomethacin to all animals (J F Long, P J S Chiu, M J Derelanko & M Steinerg, *J. Pharmacol. Expt. Ther.* 1983, 226, 114). Compound 4 (10, 20 and 50 mg/kg dose) in 0.4% HPMC were administered p.o. 45 min before the induction of ulceration by indomethacin. Six hours following the administration of indomethacin, the animals were killed, stomachs removed and opened along the greater curvature. The ulcers were scored according to Wagner et al. (K Wagner, J Nandi, R L King & R A Levine, *Dig. Dis. Sci.* 1995, 40, 134).

The effect of compound 4 was rendered graphically in terms of ulcer index and expressed as the percent protection of ulcers with that of the untreated control group.

Figure 6:
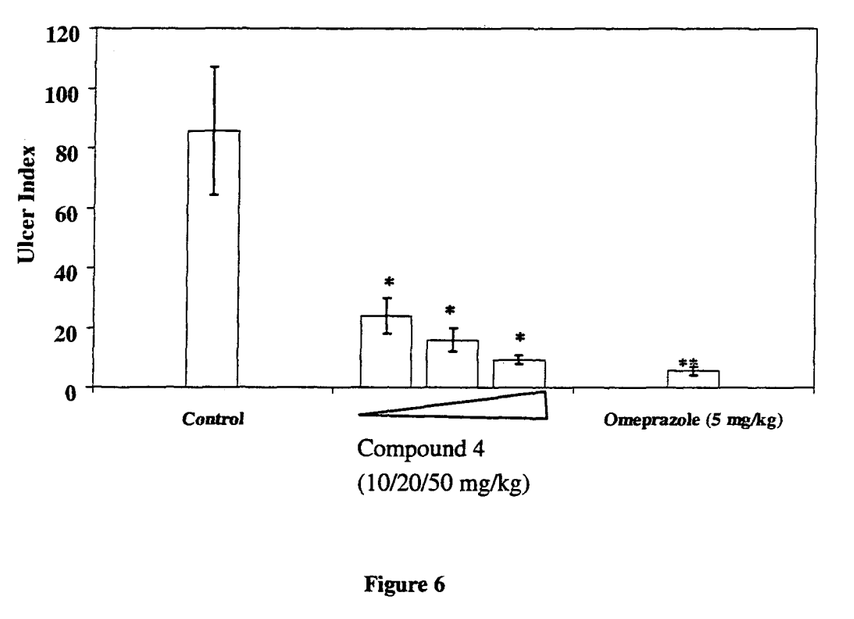
FIG. 6: Effect of compound 4 on indomethacin-induced ulcer in rat. Animals were divided into five groups. Data represent the mean±SEM (n=6). Student's unpaired t-test was carried out to evaluate the statistically significant difference of the mean of treated group from that of the untreated control. * $P<0.05$ vs. control, ** $P<0.01$ vs. control.

As described in FIG. 6, compound 4 exhibited ~75% protection of indomethacin induced ulcer formation. Omeprazole under identical experimental condition exhibited ~90% protection of ulcer formation.

The main advantages of the present invention are:
1. The steroidal compound 3-acetoxy-17-acetamido-16-formyl-androst-5,17-diene (4) exhibited its activity as gastric proton pump inhibitor (anti gastric-ulcer).
2. The steroidal compound 3-acetoxy-2'-chloro-5-androsteno[17,16-b]pyridine (5) also exhibited its activity as gastric proton pump inhibitor.
3. The steroidal derivative 4 further exhibited dose-dependent inhibition of histamine-stimulated acid secretion in parietal cell with $IC_{50}$ value comparable to cimetidine.
4. Compound 4 did not show acute toxicity in swiss albino mice at 1 g/kg dose.
5. The steroidal derivative 4 further exhibited potent anti ulcer activity against indomethacin induced ulcer at doses comparable to the known drug omeprazole.
6. Incorporation of a beta-formyl enamide and pyridine ring at steroidal D-ring via Vilsmeier reaction of steroidal D-ring enamide.
7. The oximation of 16-DPA could be accomplished in excellent yields (88-90%) in presence of potassium dihydrogen phosphate.
8. Incorporation of a 16-formyl and 17-enamide group at steroidal D-ring via synthesis from commercially available 16-DPA molecule in three major steps.
9. Incorporation of a 2'-chloro-pyridine ring at steroidal D-ring via synthesis from commercially available 16-DPA molecule in three major steps.
10. Vilsmeier reaction of 3-acetoxy-17-acetamido-androst-5,17-diene (3) carried at an ambient temperature led to a mixture of 3-acetoxy-17-acetamido-16-formyl-androst-5,17-diene (4) and 3-acetoxy-2'chloro-5-androsteno[17,16-b]pyridine (5).

We claim:
1. A method of treating peptic ulcer disease in a subject comprising:
   obtaining 3-acetoxy-17-acetamido-16-formyl-androst-5,16-diene and/or 3-acetoxy-2'chloro-5-androsteno[17,16-b]pyridine; and
   administering the 3-acetoxy-17-acetamido-16-formyl-androst-5,16-diene and/or 3-acetoxy-2'chloro-5-androsteno[17,16-b]pyridine to a subject;
   wherein the peptic ulcer disease is treated.

* * * * *

UNITED STATES PATENT AND TRADEMARK OFFICE
CERTIFICATE OF CORRECTION

| | | |
|---|---|---|
| PATENT NO. | : 8,513,226 B2 | Page 1 of 1 |
| APPLICATION NO. | : 12/935877 | |
| DATED | : August 20, 2013 | |
| INVENTOR(S) | : Romesh Chandra Boruah et al. | |

It is certified that error appears in the above-identified patent and that said Letters Patent is hereby corrected as shown below:

On the Title Page

<u>Item (56), Other Publications, line 10</u>
Change "Potter et aL," to -- Potter et al., --

<u>Item (56), Other Publications, line 22</u>
Change "Long et aL," to -- Long et al., --

Signed and Sealed this
Twenty-second Day of October, 2013

Teresa Stanek Rea
*Deputy Director of the United States Patent and Trademark Office*